United States Patent [19]

Feather

[11] 4,230,114
[45] Oct. 28, 1980

[54] EXERCISE PANTS

[76] Inventor: Jack V. Feather, P.O. Box 737, Pebble Beach, Calif. 93953

[21] Appl. No.: 882,649

[22] Filed: Mar. 2, 1978

[51] Int. Cl.³ ............................................. A61F 7/00
[52] U.S. Cl. .................................. 128/293; 128/298; 2/69; 2/227
[58] Field of Search ............... 128/1 A, 159, 160, 521, 128/518 R, 291–299, 400, 402, 401; 272/69; 2/2.1, 2.1 R, DIG. 3, 69, 227

[56] References Cited

U.S. PATENT DOCUMENTS

| | | | |
|---|---|---|---|
| 594,961 | 12/1897 | McLean et al. | 128/298 |
| 726,791 | 4/1903 | Armbruster | 128/298 |
| 3,175,560 | 3/1965 | Menzies | 128/293 |
| 3,307,554 | 3/1967 | Thornton et al. | 128/293 |
| 3,589,366 | 6/1971 | Feather | 128/293 |

FOREIGN PATENT DOCUMENTS

| | | | |
|---|---|---|---|
| 319327 | 11/1902 | France | 128/298 |
| 1178715 | 1/1970 | United Kingdom | 128/298 |
| 1245070 | 9/1971 | United Kingdom | 128/293 |

Primary Examiner—Robert W. Michell
Assistant Examiner—Arthur S. Rose
Attorney, Agent, or Firm—Bruce & McCoy

[57] ABSTRACT

A pair of exercise pants comprised of pant material which throughout its length and width is non-porous and non-absorbent, said pants having cinching elements for cinching the pant material about the waist and legs of the user in a manner which substantially pneumatically isolates the interior of the pants from outside atmosphere, and said pants further including an evacuation hose connector sealedly secured to the pant material at the rear seat portion thereof whereby when the user exercises, such as by running in place, air can be evacuated from the interior of the pants causing the pant material to press against the user's body to induce midsection sweating thereby promoting overall girth reduction.

6 Claims, 5 Drawing Figures

U.S. Patent     Oct. 28, 1980     4,230,114
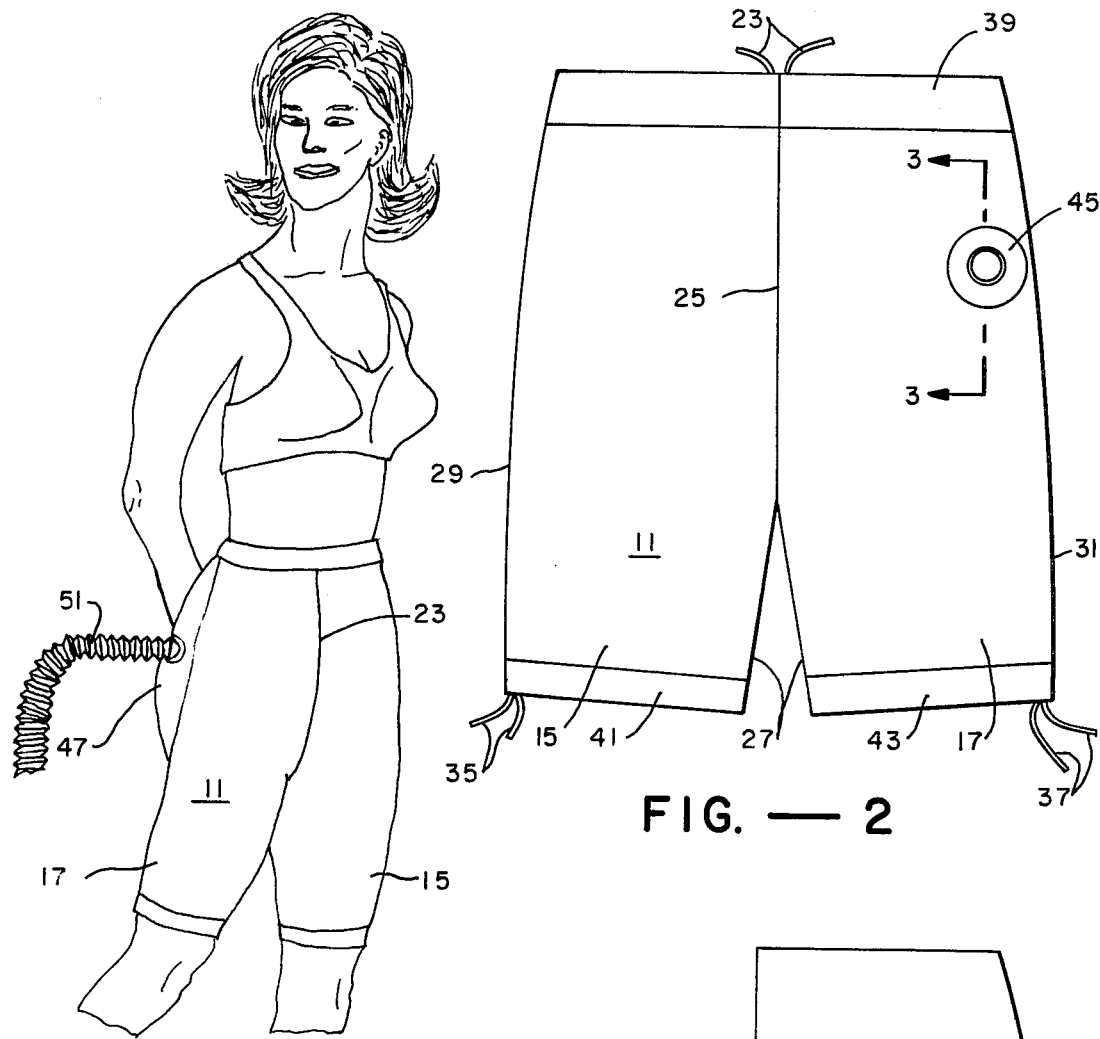
FIG. — 1
FIG. — 2
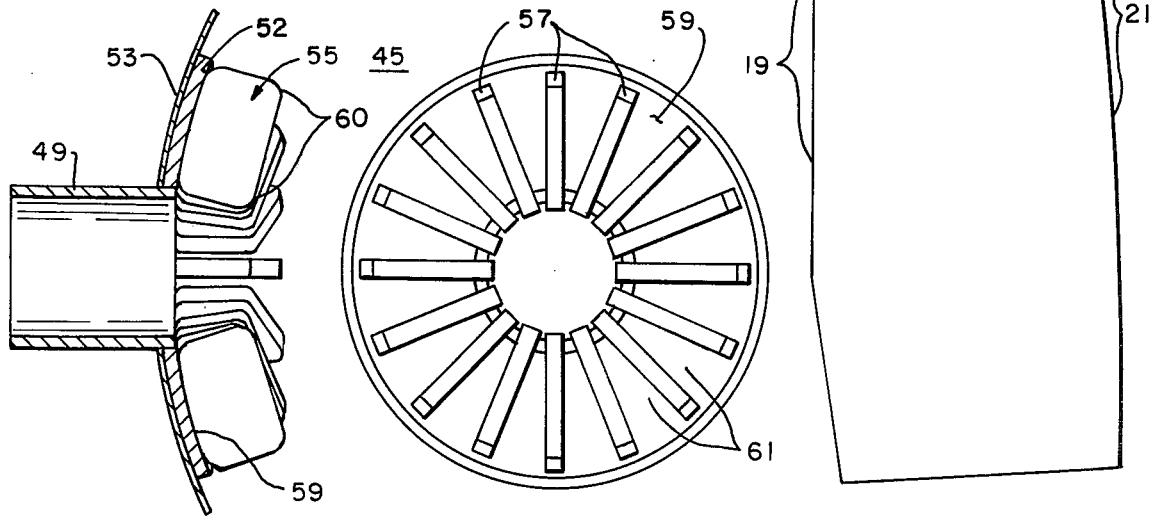
FIG. — 3     FIG. — 4     FIG. — 5

EXERCISE PANTS

BACKGROUND OF THE INVENTION

1. Field of the Invention

The present invention relates to exercising aids, and more particularly to exercising pants which when properly used by the wearer are adapted to promote girth reduction.

2. Description of the Prior Art

Heretofore, pants used to promote weight and girth reduction have been of an inflatable type wherein inflation of the pants causes a continuous increased pressure against the body of the wearer to provide pressure against the wearer's muscles when the wearer exercises. Such pants are illustrated in British Pat. Specification No. 1,245,070, published Sept. 2, 1971. The inflatable pants disclosed in this patent show a variety of ribs, panels, and securement belts all designed to maintain as even a pressure as possible over the covered areas of the body.

The present invention provides a concept of exercise pants entirely different of that shown in British Pat. Specification No. 1,245,070, in that it is contemplated that, instead of pressurizing pants, air will be evacuated from the interior of the pants to cause the pant material, chosen for its desired moisture retention qualities, to tightly adhere to the body surfaces by external atmospheric pressure. Because atmospheric pressure is uniform throughout, the pressure holding the pant material against the body surfaces will be uniform throughout so long as interior pressure pockets are substantially eliminated through air evacuation. The present invention also has this feature of providing a pair of exercise pants wherein the pants can be manufactured in one large size to fit persons of substantially all sizes.

When the exercise pants of the present invention are worn by the user, the user is free to perform exercises, such as running in place, while air evacuation within the pants is maintained. It is believed that with properly chosen materials the pant material which tightly surrounds the covered parts of the body will induce sweating in these parts and promote overall girth reduction.

SUMMARY OF THE INVENTION

The present invention is a pair of exercise pants comprising a pant material which throughout its length and width is non-porous and non-absorbent. Means are provided for sealedly cinching the pant material about the waist and legs of the user whereby the space between the pant material and the user's body is substantially pneumatically isolated from outside atmosphere. Connector means, sealedly secured to the pant material, are adapted to permit an air evacuation hose to be attached thereto whereby when the user exercises, such as by running in place, air can be evacuated from the interior of the pants causing the pant material to press against the user's body to induce sweating thereby producing overall girth reduction.

OBJECTS OF THE INVENTION

It is therefore an object of the present invention to provide a pair of exercise pants which when properly used by the wearer will promote overall reduction in body girth.

It is another object of the present invention to provide a pair of exercise pants which are easily donned by the user to facilitate a home exercise and weight reduction program.

It is a further object of the present invention to provide a pair of exercise pants which can have its interior air evacuated by conventional household vacuum cleaner.

It is still another object of the present invention to provide a pair of exercise pants which eliminate the multiplicity of securement straps which are used in conventional inflatable weight reducing pants.

It is still a further object of the present invention to provide a pair of exercise pants which can be fabricated from a minimum amount of material panels, securement elements, and pneumatic connector elements at a very low cost.

It is yet another object of the present invention to provide a pair of exercise pants which can be manufactured in one size which substantially all users regardless of size can wear.

Yet other objects of the present invention will become apparent from the following specification and claims.

DESCRIPTION OF THE DRAWINGS

FIG. 1 is a pictorial view of a women wearing the exercise pants according to the present invention.

FIG. 2 is a rear elevational view of the exercise pants of the present invention showing the placement of the invention's air evacuation hose conector.

FIG. 3 is a cross-sectional view of the connector shown in FIG. 2 taken along lines 3—3.

FIG. 4 is a rear elevational view of the connector shown in FIG. 3 as seen from the interior of the exercise pants.

FIG. 5 is a front elevational view of a material panel used in the fabrication of the exercise pants shown in FIGS. 1 and 2.

DESCRIPTION OF THE PREFERRED EMBODIMENT

Referring now to the drawings, the exercise pants of the present invention are generally designated by the numeral 11. The pants are of the bermuda type which encircle the user's waist at their top end 13, and which at their leg ends 15, 17 encircle the legs of the user somewhat above the knee. The pant is fabricated from a non-porous and non-absorbent material which extends throughout the length and width of the pant to provide non-absorbency over that entire inside surface which comes in contact with the wearer's body. A suitable pant material is polyvinyl plastic sheet, however, it is contemplated that other non-porous and non-absorbent sheet materials could be used.

The pants can be made from four nearly identical panels of material, with the shape of each panel being generally illustrated in FIG. 5. The lateral edges 19, 21 of the four panels are joined respectively at the front 23 and seat 25 of the pants, through the inside legs and crotch 27, and along the pants sides 29, 31. The joined edges are hermetically sealed, such as by a heat seal, whereby the entire pant is continuously non-porous and capable of holding the moisture produced by the wearer's body as the wearer performs exercises.

As seen in FIG. 1 the exercise pants of the present invention, when worn, are tightly cinched about the user's legs and waist to as nearly as possible pneumatically isolate the space between the pant material and the user's body from outside atmosphere. Suitably tight cinching can be achieved by providing elastic drawstrings 33, 35, 37 threaded through casings 39, 41, 43 in the pant waist and each of the pant leg ends. Other cinching means might also be employed such as an elastic material having Velcro tabs at the outer ends.

Other than providing a means for tightly cinching the pants around the user's leg and waist, the concept of "fit" is not especially important to the present invention. In fact, the pants should be made with enough material such that, when they are cinched to the body, there will be enough material to accommodate the girth of any potential user whose girth and stature is not unusually large. Thus, the pant can be made such that one size can fit all, or most all persons, regardless of the size of the wearer. The pant material will tightly press against the user's body by evacuating air from the interior of the pants in the manner described below.

A pneumatic connector means 45 is sealedly secured to the pant material, with the connector means preferably being located in the rear seat portion of the pants. Referring to FIG. 2, the preferred position of the connector 45 is shown as being nearest the lateral side 31 of the pants and approximately midway between the top and the bottom of the pant seat portion 47 covering the buttocks of the user. The connector, which can be a molded plastic part, is comprised of a projecting section of non-threaded tubing 49 adapted to mate with an air evacuation hose 51, such as the extension of a vacuum cleaner hose; the connector also has a slightly cupped base portion 52 which supports the tubing 49 and onto which the pant material 53 can be sealedly secured, such as by gluing or heat sealing. By connecting a conventional vacuum cleaner to the connector 45 of the exercise pants 11 through a suitably long extension hose 51, air can be continuously evacuated from the interior of the pants while the user exercises, such as by running in place. The continuous evacuation of air will cause the pant material to press against the user's body to induce sweating during the exercise routine with the effect that overall girth reduction is promoted.

The pants connector 45 is provided with a bolster 55 for holding the connector means 45 together with the pant material 53 immediately surrounding the connector means away from the user's body during the period of time when the air is being evacuated from the interior of the pants. This prevents the connector means from sucking down onto the skin of the wearer as a result of the vacuum pressure, an occurance which in addition to creating discomfort to the user would inhibit the air evacuation from the remaining portions of the pants. The bolster 55 must be of a design which permits air permeability therethrough while at the same time holding the connector end surrounding material substantially away from the user's body. As shown in FIGS. 3 and 4 the bolster in its preferred embodiment consist of plurality of radially disposed flanges 57 which project inwardly from the interior surface 59 of the connector base 51; the flanges are thus disposed in perpendicular relation to the connector base and the pant material surrounding the connector base. This configuration permits air to flow in through the radially diverging channels 61 as defined by the flange's sides while the projecting flange edges bear against the user's body. For comfort, the projecting flange corners 60 should be rounded and the flanges sufficiently numerous to spread out contact pressure.

To use the exercise pants of the present invention, the user simply first steps into the pants and then cinches the pants tightly about his or her waist and legs by tying the respective drawstrings 33, 35, 37. Air evacuation extension hose 51 is then attached to the pant connector 45 and the air evacuation pump activated. Once the air in the interior of the pants is sufficiently evacuated to cause the pant material to press firmly against the user's skin, the user performs any suitable stationary exercise. The pants, because of their non-porosity and non-absorbency, will induce the user to sweat in the covered areas and will thereby, it is believed, promote girth reduction. When the user finishes exercising, the air evacuation pump is deactivated and the extension hose disconnected whereupon the pants can be removed. It is noted that the exercise pants should be used with a minimum amount of undergarment, and preferably no undergarment, in order to eliminate material of any absorbency from around the body surface portions underlying the pant material.

The present invention therefore is a pair of exercise pants designed to permit the air from the interior portion of the pants to be evacuated thereby causing the pant material to press against the user's body surfaces underlying the pants for inducing sweating over that portion of the body. The exercise pants of the present invention are used in connection with an exercise program for the purpose of promoting the reduction of body girth. Although the present invention has been described in considerable detail in the foregoing specification, it is not intended that the invention be limited to such detail, except as necessitated by the appended claims.

What I claim is:

1. A pair of exercise pants comprising a pant material which throughout its length and width is non-porous and non-absorbent, means for cinching said pant material about the waist and legs of the user whereby the space between the pant material and the user's body is substantially pneumatically isolated from outside atmosphere, and connector means sealedly secured to said pant material, said connector means being adapted to permit an air evacuation hose to be attached thereto whereby when the user exercises, such as by running in place, air can be evacuated from the interior of said pants causing the pant material to press against the user's body to induce sweating and to thereby promote overall girth reduction, wherein said connector means includes an air permeable bolster means disposed on the internal side of said pants for holding said connector means together with the pant material immediately surrounding same away from the user's body surfaces whereby the connector means and surrounding pant material are prevented from bearing down onto the user's skin while air is being evacuated from the interior of said pants.

2. The exercise pants of claim 1 wherein said air permeable bolster means includes a plurality of radially disposed flanges projecting inwardly in substantial perpendicular relation to said pant material.

3. A pair of exercise pants comprising a pant material which throughout its length and width is non-porous and non-absorbent, said pants being adapted to extend from the user's midsection down over at least a portion of the user's thighs, means for sealedly cinching said pant material about the waist and legs of the user whereby the space between the pant material and the user's body is substantially pneumatically isolated from outside atmosphere, and a connector means sealedly secured to said pant material at the rear seat portion of said pants, said connector means adapted to permit an air evacuation hose to be attached thereto whereby when the user exercises, such as by running in place, air can be evacuated from the interior of said pants causing the pant material to press against the user's body to induce sweating and to thereby promote overall girth reduction, said connector means including an air permeable bolster means disposed on the interior side of said pants for holding said connector means together with the pant material immediately surrounding same away from the user's body surfaces whereby the connector means and surrounding pant material are prevented from bearing down onto the user's body as a result of air evacuation.

4. The exercise pants of claim 3 wherein said air permeable connector bolster means includes a plurality of radially disposed flanges projecting inwardly in substantial perpendicular relation to said pant material.

5. The exercise pants of claim 4 wherein said connector means is located to the lateral side and approximately at the middle of the pant rear seat portion.

6. The exercise pants of claim 5 wherein the pants are sized such that one size will accommodate the girth of most users.

* * * * *